(12) United States Patent
Vivanz et al.

(10) Patent No.: US 10,898,348 B2
(45) Date of Patent: Jan. 26, 2021

(54) SURGICAL SHOULDER ARTICULATION REPLACEMENT METHOD

(71) Applicant: Tornier, Montbonnot-Saint-Martin (FR)

(72) Inventors: Willy Vivanz, Crolles (FR); Jean-Emmanuel Cardon, Domene (FR)

(73) Assignee: Tornier, Montbonnot-Saint-Martin (FR)

( * ) Notice: Subject to any disclaimer, the term of this patent is extended or adjusted under 35 U.S.C. 154(b) by 166 days.

(21) Appl. No.: 15/835,110

(22) Filed: Dec. 7, 2017

(65) Prior Publication Data

US 2018/0161176 A1     Jun. 14, 2018

Related U.S. Application Data

(60) Provisional application No. 62/433,492, filed on Dec. 13, 2016.

(51) Int. Cl.
*A61F 2/46*     (2006.01)
*A61F 2/30*     (2006.01)
(Continued)

(52) U.S. Cl.
CPC ........ *A61F 2/4612* (2013.01); *A61B 17/1778* (2016.11); *A61F 2/30771* (2013.01); *A61F 2/30942* (2013.01); *A61F 2/4059* (2013.01); *A61F 2/30721* (2013.01); *A61F 2/4657* (2013.01); *A61F 2002/3082* (2013.01); *A61F 2002/30113* (2013.01); *A61F 2002/30125* (2013.01); *A61F 2002/30593* (2013.01); *A61F 2002/30616* (2013.01); *A61F 2002/30617* (2013.01); *A61F 2002/30718* (2013.01); *A61F 2002/30784* (2013.01);

(Continued)

(58) Field of Classification Search
CPC . A61F 2/4612; A61F 2/30771; A61B 17/1778
See application file for complete search history.

(56) References Cited

U.S. PATENT DOCUMENTS 4,101,985 A * 7/1978 Baumann ............ A61F 2/30739
                                                         606/67
4,549,319 A * 10/1985 Meyer ................. A61F 2/30734
                                                         606/100
(Continued)

FOREIGN PATENT DOCUMENTS

EP      0 721 767     7/1996
EP      0 765 644     4/1997
(Continued)

OTHER PUBLICATIONS

Extended European Search Report issued in EP Application No. 17206573.2, dated May 18, 2018, in 7 pages.

*Primary Examiner* — Bruce E Snow
*Assistant Examiner* — Melissa A Hoban
(74) *Attorney, Agent, or Firm* — Knobbe Martens Olson & Bear, LLP (57) ABSTRACT

A surgical shoulder articulation replacement method is provided. The method can include providing a humeral implant having a hollow stem. The hollow stem can be provided with a sharp distal edge. The method can include impacting the humeral implant in a cancellous bone of a humeral head of a patient, with the sharp distal edge cutting the cancellous bone in the process.

20 Claims, 8 Drawing Sheets (51) Int. Cl.
*A61F 2/40* (2006.01)
*A61B 17/17* (2006.01)

(52) U.S. Cl.
CPC ............... *A61F 2002/30845* (2013.01); *A61F 2002/30962* (2013.01); *A61F 2002/4062* (2013.01); *A61F 2002/4658* (2013.01); *A61F 2002/4663* (2013.01); *A61F 2002/4681* (2013.01); *A61F 2002/4687* (2013.01)

(56) References Cited

U.S. PATENT DOCUMENTS

| | | | | |
|---|---|---|---|---|
| 4,904,262 | A * | 2/1990 | Bensmann | A61F 2/3662 623/23.44 |
| 5,032,134 | A * | 7/1991 | Lindwer | A61F 2/30734 623/23.36 |
| 5,047,060 | A * | 9/1991 | Henssge | A61F 2/36 623/22.46 |
| 5,092,899 | A * | 3/1992 | Forte | A61F 2/30767 623/23.32 |
| 5,152,798 | A * | 10/1992 | Kranz | A61F 2/3662 623/23.33 |
| 5,156,628 | A * | 10/1992 | Kranz | A61F 2/30771 623/23.33 |
| 5,316,550 | A * | 5/1994 | Forte | A61F 2/30767 623/23.32 |
| 5,330,536 | A * | 7/1994 | Tager | A61F 2/3662 623/23.33 |
| 5,480,453 | A * | 1/1996 | Burke | A61B 17/1604 623/23.21 |
| 5,658,352 | A * | 8/1997 | Draenert | A61B 17/8808 623/22.4 |
| 5,725,592 | A * | 3/1998 | White | A61F 2/36 623/23.35 |
| 5,871,549 | A * | 2/1999 | Jayashankar | A61F 2/30767 623/22.4 |
| 5,976,137 | A * | 11/1999 | Mayer | A61B 17/1659 606/300 |
| 6,093,209 | A | 7/2000 | Sanders | |
| 6,391,031 | B1 * | 5/2002 | Toomey | A61B 17/15 606/82 |
| 7,001,392 | B2 * | 2/2006 | McGovern | A61B 17/164 606/80 |
| 7,390,327 | B2 * | 6/2008 | Collazo | A61B 17/1675 606/88 |
| 8,778,030 | B2 | 7/2014 | Sidebotham | |
| 2001/0047210 | A1 * | 11/2001 | Wolf | A61B 17/15 623/19.14 |
| 2005/0125067 | A1 * | 6/2005 | Sweeney | A61F 2/36 623/19.14 |
| 2012/0010722 | A1 * | 1/2012 | Walter | A61F 2/3601 623/23.18 |
| 2012/0296339 | A1 * | 11/2012 | Iannotti | A61B 17/15 606/87 |
| 2013/0114873 | A1 * | 5/2013 | Chaoui | G06K 9/4638 382/131 |
| 2013/0304228 | A1 | 11/2013 | Phipps | |
| 2014/0330390 | A1 * | 11/2014 | Liu | A61F 2/3662 623/23.21 |
| 2016/0000579 | A1 | 1/2016 | Ramachandran et al. | |
| 2016/0015380 | A1 * | 1/2016 | Sholev | A61B 17/0482 606/80 |
| 2016/0143749 | A1 * | 5/2016 | Holovacs | A61F 2/4081 623/19.11 |
| 2016/0324648 | A1 * | 11/2016 | Hodorek | A61F 2/4003 |
| 2017/0304063 | A1 * | 10/2017 | Hatzidakis | A61B 17/68 |

FOREIGN PATENT DOCUMENTS

| | | |
|---|---|---|
| EP | 2 502 605 | 9/2012 |
| WO | WO 2006/052874 | 5/2006 |

* cited by examiner

SURGICAL SHOULDER ARTICULATION REPLACEMENT METHOD

The present invention concerns a surgical shoulder articulation replacement method.

Current surgical techniques for shoulder articulation replacement include several successive steps including reaming the humeral head, making an entry into the bone, preparing the bone including punching, compacting, fixing an implant, protecting the implant, making a trial articulation mounting and mounting the final implant. All these preparation steps are long and costly. Moreover, the known techniques which use patient specific implants or ranges of implants also need patient specific or ancillary tools such as rasps, drills and cutting guides, whose manufacturing and shipping is costly.

A goal of the invention is to provide a new surgical method for shoulder articulation replacement which is more simple, and less costly than the techniques of the prior art.

To this end, the invention concerns a surgical shoulder articulation replacement method consisting of:
  a) providing a humeral implant having a hollow stem, said hollow stem being provided with a sharp distal edge,
  b) impacting the humeral implant in a cancellous bone of a humeral head of a patient, with the sharp distal edge cutting the cancellous bone in the process.

Thanks to the invention, the long and costly bone preparation steps and ancillary tools are no more needed, as the implant is directly impacted into the bone, creating a hole in the bone.

The invention also concerns a surgical shoulder articulation replacement method consisting of:
  a) determining the size and shape of a humeral implant using imaging,
  b) providing the humeral implant with a hollow stem, said hollow stem having a sharp distal edge,
  c) impacting the humeral implant in a cancellous bone of a humeral head of a patient, with the sharp distal edge cutting the cancellous bone in the process.

The invention further concerns a surgical shoulder articulation replacement method consisting of:
  a) conducting pre-operation imaging on a patient so as to determine a patient-specific size and shape for a humeral implant comprising a hollow stem having a sharp distal edge,
  b) manufacturing the humeral implant having the patient-specific size and shape, using additive manufacturing,
  c) impacting the humeral implant in a cancellous bone of a humeral head of a patient, with the sharp distal edge cutting the cancellous bone in the process.

According to further aspects of the invention which are advantageous but not compulsory, such a surgical method may incorporate one or several of the following features:
  the method further comprises a step consisting of attaching an articulation member on the humeral implant,
  the method comprises a further step, prior to step a), consisting of determining the size and shape of the humeral implant using imaging,
  the size and shape of the humeral implant are determined by imaging,
  the method comprises a step consisting of providing an insertion guide adapted to guide the impaction of the humeral implant,
  prior to step b), the method comprises a step consisting of making a cut in a cortical bone of the humeral head so as to uncover the cancellous bone,
  the method comprises a further step consisting of holding the humeral implant with a holding tool fixed to the humeral implant and having a handle,
  the method comprises a further step consisting of impacting the holding tool with a striking instrument,
  the method comprises a further step consisting of impacting the humeral implant with a striking instrument,
  the method comprises a further step consisting of impacting a detachable portion of the humeral implant with a striking instrument, then removing the detachable portion once the humeral implant is at its final place in the bone,
  the method comprises a further step consisting of providing a set of humeral implants of different sizes and shapes,
  the hollow stem has a circular cross section,
  the hollow stem has an ovoid cross section,
  the hollow stem of the humeral implant is pierced with transversal holes,
  the humeral implant is made by additive manufacturing,
  the humeral implant is manufactured in titanium or titanium alloy,
  the method comprises a step consisting of making a reference mark on the bone corresponding to the desired location of impaction of the sharp distal edge of the hollow stem,
  the reference mark is provided by a reference punch matching the shape of the sharp distal edge of the hollow stem and adapted to create a groove in the bone.

The invention will now be explained in reference to the annexed drawings, as an illustrative example. In the annexed drawings.

Figure 1:
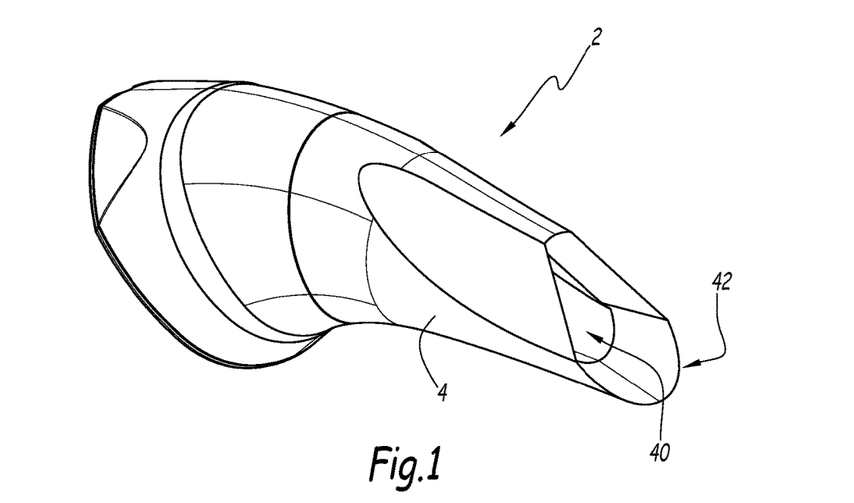
FIG. 1 is a perspective view of a humeral implant with which the method of the invention can be operated.

FIG. 1 shows a humeral implant 2 having a hollow stem 4 with which a surgical shoulder articulation replacement method is operated. In other words, this surgical method includes a step of providing the humeral implant.

Figure 2:
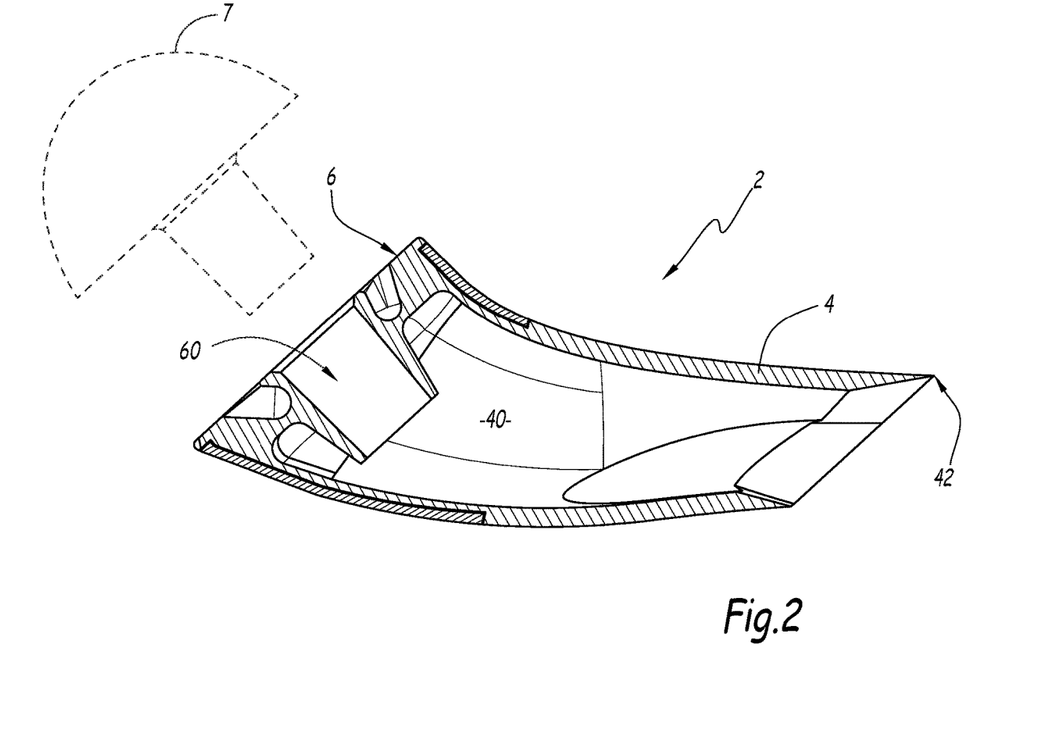
FIG. 2 is a cross-sectional view of the humeral implant of FIG. 1.

As represented on FIG. 2, the hollow stem 4 forms an interior channel 40. The humeral implant 2 comprises a mounting surface 6, adapted to receive an articulation member 7 which is fixed on the mounting surface 6 by any convenient means. The mounting surface 6 comprises a mounting hole 60 which communicates with the interior channel 40. On the opposed side of the humeral implant 2 with respect to the mounting surface 6, the hollow stem 4 is provided with a sharp distal edge 42. The word "distal" is here used is the sense that the edge 42 is located on the far side of the humeral implant 2 with respect to the user, or/and surface intended to emerge from the bone, in other words the mounting surface 6. In an embodiment, the sharp distal edge 42 may form a continuous contour which forms the end of the interior channel 40.

In an embodiment, the method further comprises a pre-op planning/imaging step, which is operated prior to the step of providing the humeral implant 2 and which consists of determining the size and shape of the implant 2 using imaging. The imaging may include CT scans, MRI or any other convenient imaging technique. In one embodiment, the implant may have a radius of curvature (along a longitudinal axis), which is determined in the pre-op planning/imaging.

In an embodiment, the humeral implant 2 may be made by additive manufacturing. This allows providing the humeral implant 2 with a non-tubular shape, for example a curved hollow shape as represented on the figures, or any other shape determined on the basis of the shape of the humeral head of the patient. For example, the implant may be manufactured by metal powder bed fusion technologies.

Of course, other manufacturing processes may be considered for obtaining the humeral implant 2.

In an embodiment, the humeral implant 2 is manufactured in titanium or titanium alloy.

In an embodiment, the humeral implant 2 may be manufactured in its final shape in a single operation. The implant 2 does not need complementary machining operations to obtain its final shape.

The method may provide to provide a set of humeral implants 2 of different sizes and shapes. The surgeon may choose between the different sizes and shapes depending on the shape and size of the humeral head 1 of the patient determined by imaging techniques.

Alternatively, the humeral implant 2 may be patient-specific sized and shaped and directly manufactured in its patient-specific final state by additive manufacturing, to best fit to the shoulder articulation of the patient.

Figure 3:
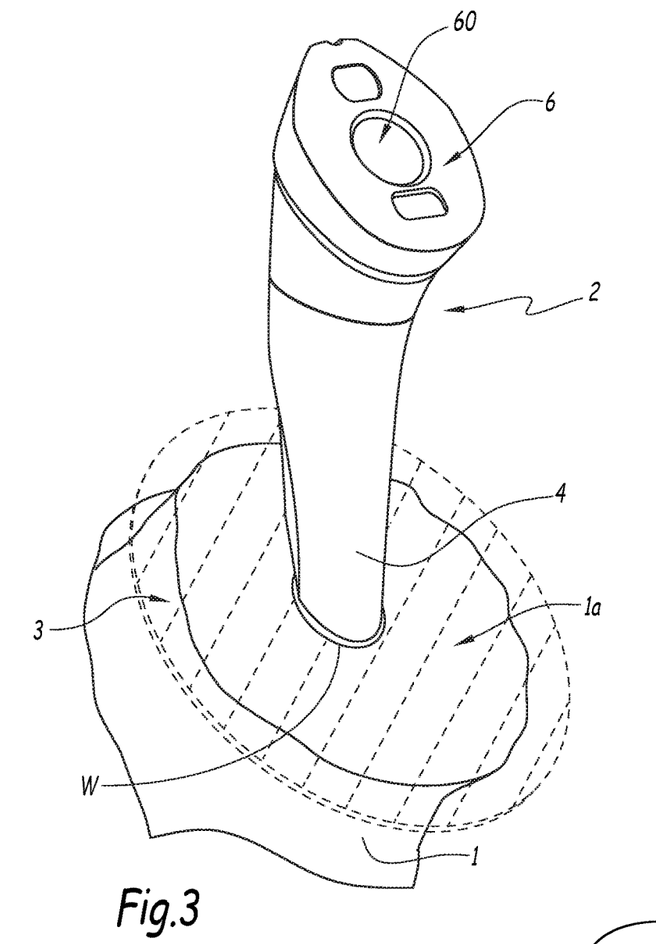
FIG. 3 is a perspective view of a humeral implant being impacted on the humeral head.
Figure 4:
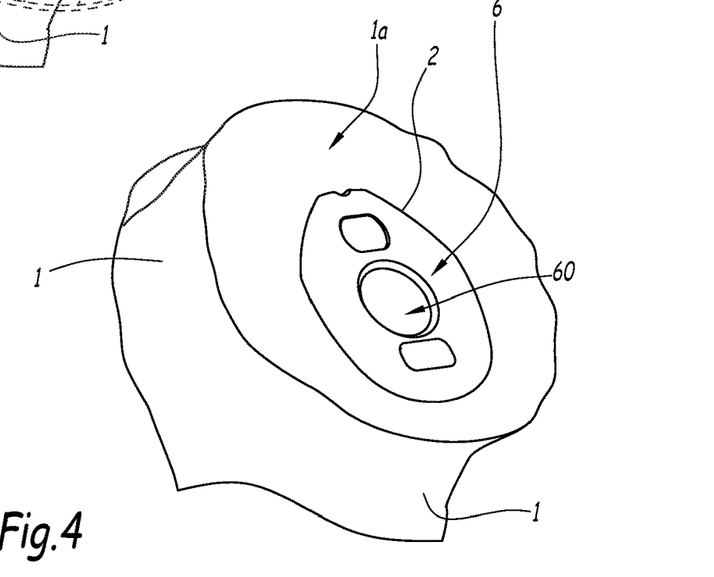
FIG. 4 is a perspective view of a humeral head with its inserted humeral implant.
Figure 5:
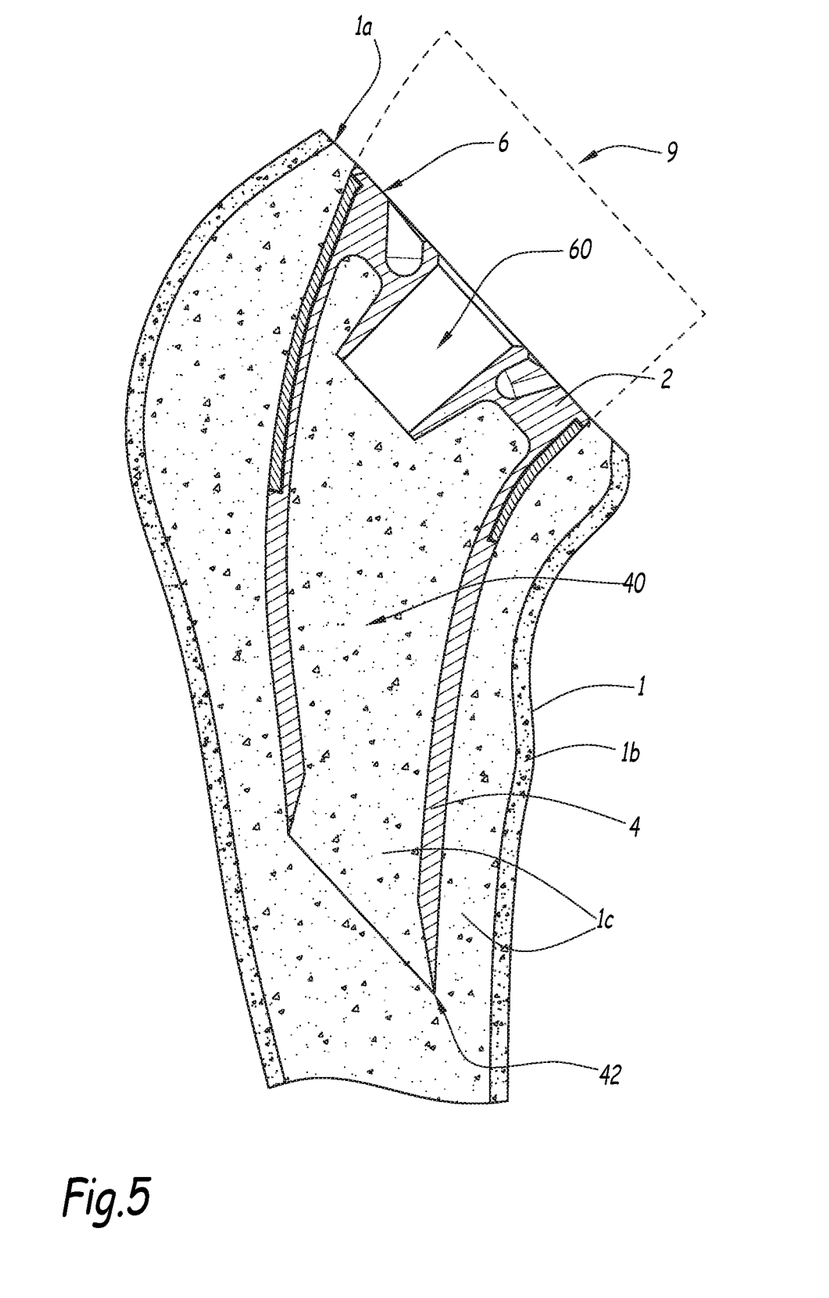
FIG. 5 is a cross-sectional view of the humeral implant inserted in the humeral head.

FIG. 3 shows a step of the surgical method consisting in impacting the humeral implant 2 into a cancellous bone 1c portion of a humeral head 1, with the sharp distal edge 42 cutting the cancellous bone 1c in the process. The sharp distal edge 42 either cuts or compacts the cancellous bone 1c, allowing a portion of the cancellous bone 1c to insert itself in the interior channel 40, creating space for the progression of the humeral implant 2 in the humeral head 1, until the articulation surface 6 is flush with a resected surface 1a of the humeral head 1, as represented on FIG. 4. The outer and inner shapes of the hollow stem 4 are designed so that the cancellous bone 1c is driven towards the mounting surface 6 during impaction. When impaction and insertion of the humeral insert 2 are completed, the interior channel 40 is fully or partially filled with cancellous bone 1c.

The method may consist of impacting the humeral implant 2 with a non-shown striking instrument, such as a hammer, by striking the implant 2 directly on the articulation surface 6.

Figure 6:
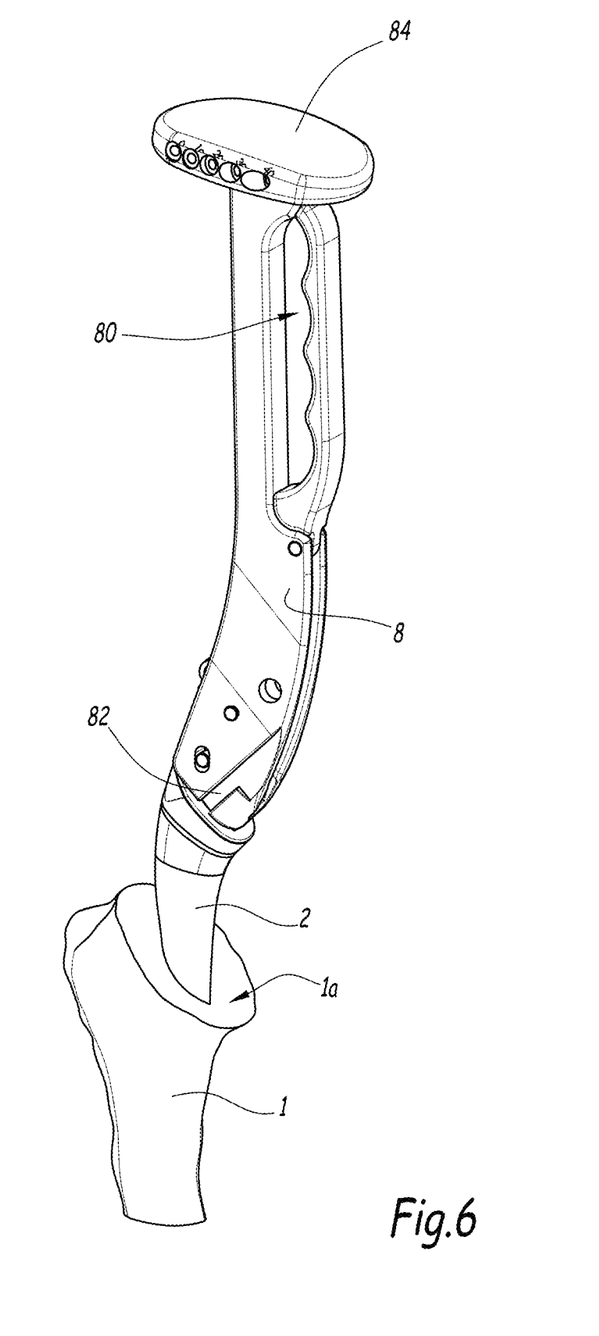
FIG. 6 is a perspective view of a first step of inserting the humeral implant in a humeral head, with a holding tool.
Figure 7:
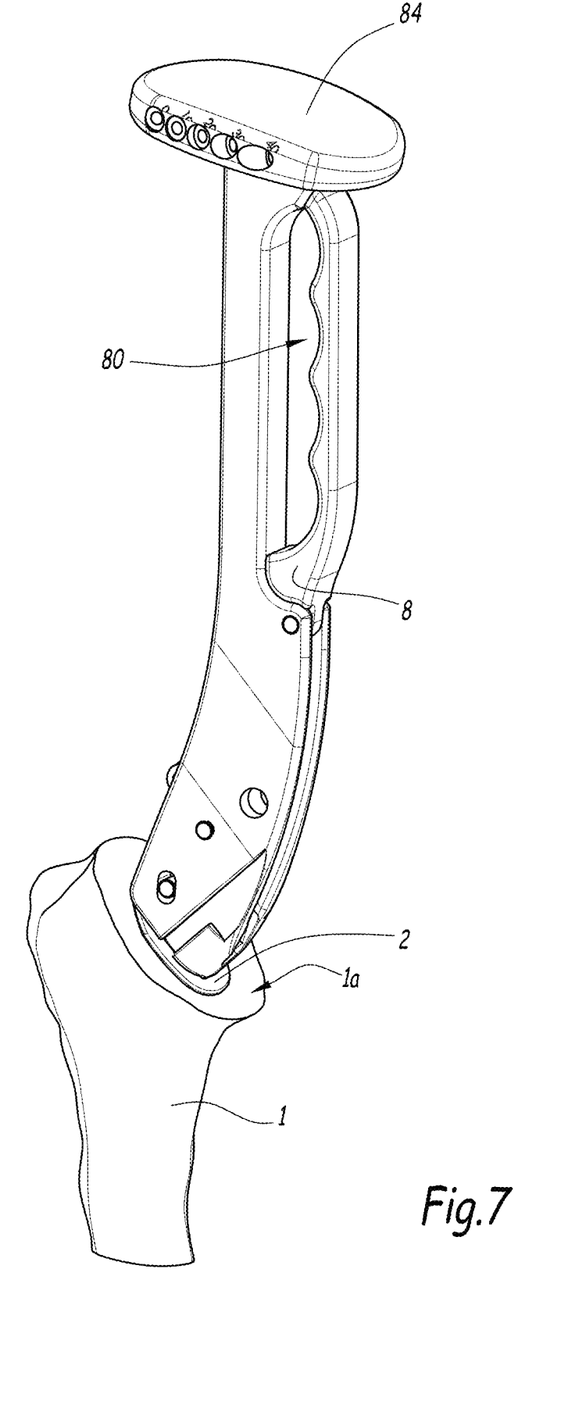
FIG. 7 is a perspective view of a final step of inserting the humeral implant in the humeral head with the holding tool of FIG. 6.

In an alternative optional embodiment represented on FIGS. 6 and 7, the method consists of holding the humeral implant 2 with a holding tool 8 including a handle 80 and means 82 for fastening the holding tool 8 with the humeral implant 2.

In an embodiment, the method may consist of impacting the holding tool 8 with a non-shown striking instrument, such as a hammer. The holding tool 8 may comprise a flat top surface 84 provided for striking the holding tool 8 with a hammer.

In an optional embodiment, the method may consist of impacting a detachable portion 9 of the humeral implant 2 with a striking instrument, then removing the detachable portion 9 once the humeral implant 2 is at its final place in the bone. The detachable portion 9 may be, for example, a part manufactured together with a main body of the humeral implant, or another part mounted on the mounting surface 6 and provided to protect the mounting surface 6 during transport and/or impaction.

In an embodiment, the method further comprises a step consisting of attaching the non-shown articulation member on the mounting surface 6 of the humeral implant 2.

Prior to impacting the humeral implant 2 in the humeral head 1, the method may comprise a step consisting of making a cut in a cortical bone portion 1b of the humeral head 1, so as to uncover the cancellous bone 1c, and provide a flat resected surface 1a.

In a non-shown embodiment; the hollow stem 4 of the humeral implant 2 may be pierced with transversal holes. The cancellous bone 1c may get inside the interior channel 40 during impaction of the humeral implant 2 via the transversal holes.

In an embodiment, the hollow stem 4 may have a circular cross-section or an ovoid cross-section.

As represented on the figures, the humeral implant 2 may have an increasing transversal section from the sharp distal edge 42 to the mounting surface 6. In non-shown alternatives, the transversal section of the humeral implant 2 may have different progression profiles.

In some embodiment, the method may comprise a step consisting of providing an insertion guide 3 adapted to guide the impaction of the humeral implant 2. Such insertion guide 3 may include, for example, an insertion window Win which the humeral implant 2 is inserted during impaction so that the humeral implant 2 follows the right path for the intended final position of the humeral implant 2.

In an optional embodiment represented on FIGS. 8 to 13, the method may include a step consisting in making a reference mark on the humeral head 1 corresponding to the desired location of impaction of the sharp edge 42 of the hollow stem 4. Such step may help a non-specialist surgeon to find the best position for insertion of the hollow stem 4.

Figures 8, 9, 10, 11:
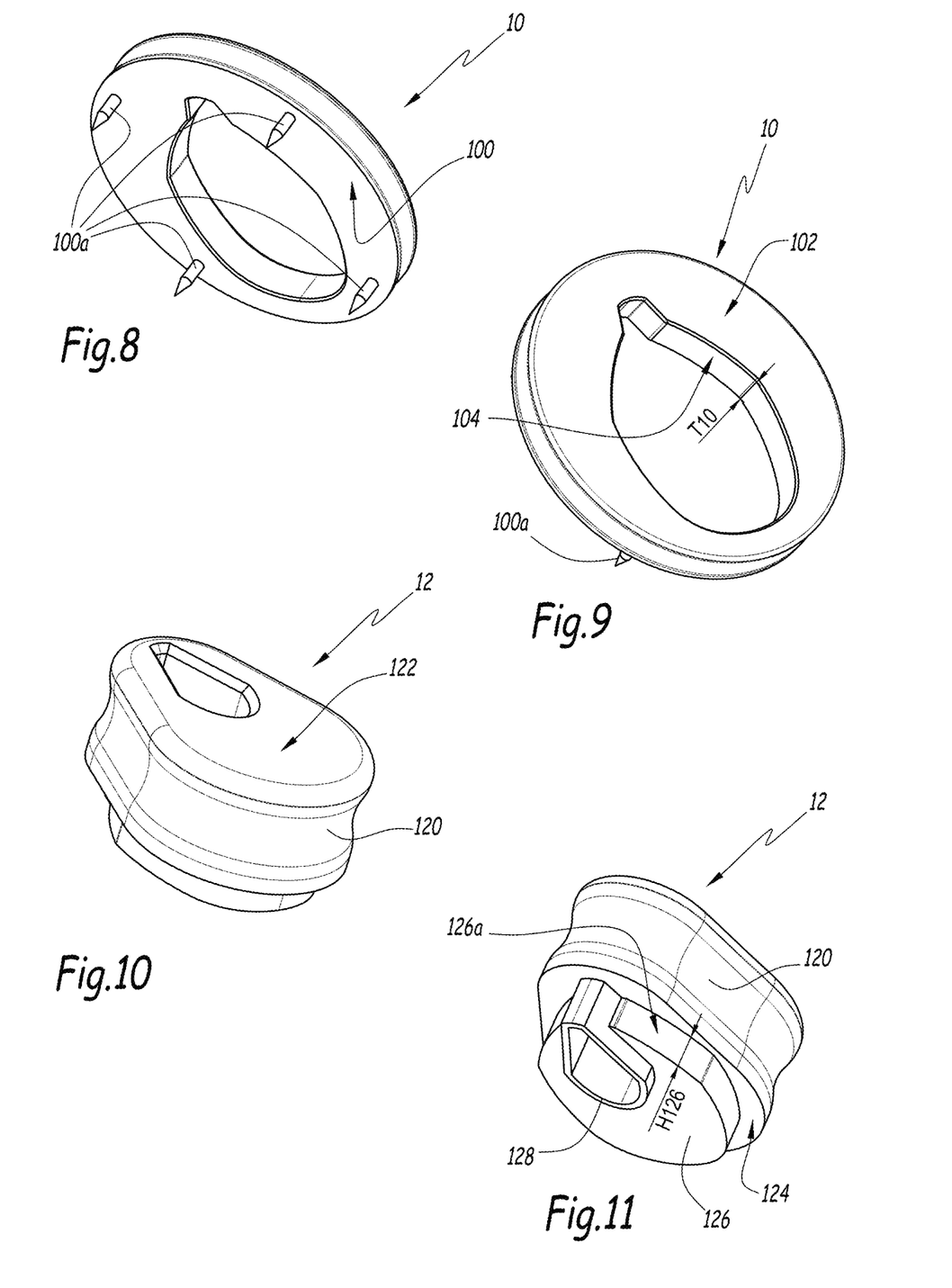
FIG. 8 is a perspective view of a positioning tool used in the method of the invention.
FIG. 9 is a perspective view from an opposed angle, of the positioning tool of FIG. 6.
FIGS. 10 and 11 are perspective views, from two different angles, of a reference punch used in the method of the invention.
Figure 12:
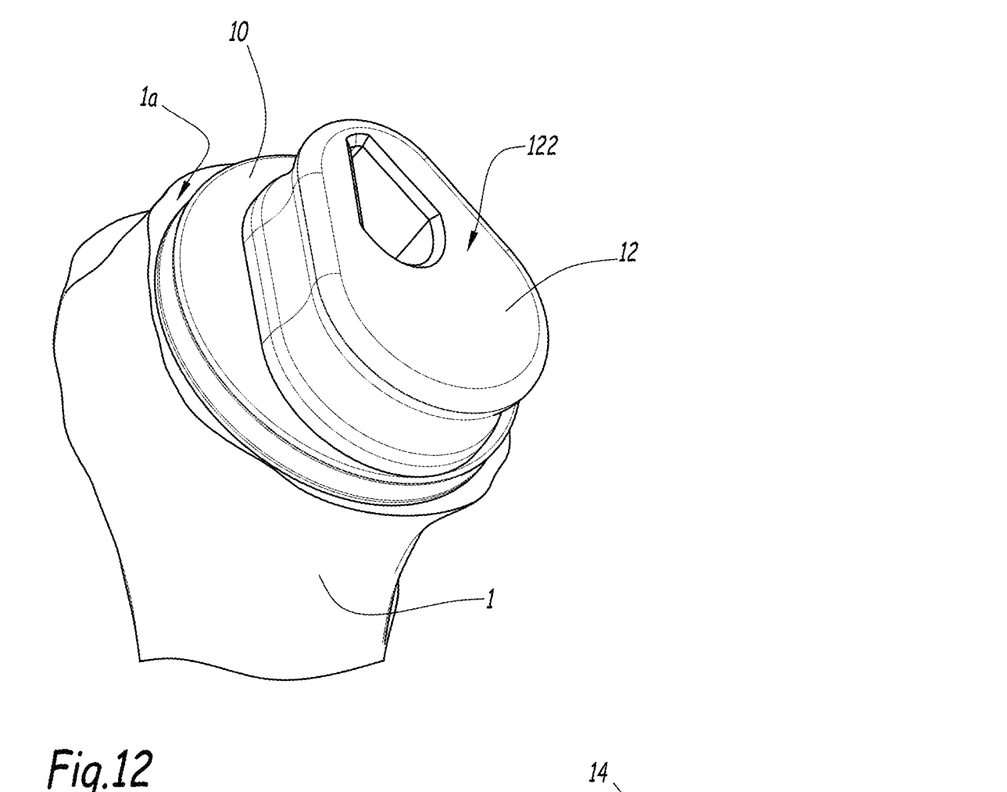
FIG. 12 is a perspective view of a step of creating a reference mark on a humeral head using the positioning tool of FIGS. 8 and 9 and the reference punch of FIGS. 10 and 11.
Figure 13:
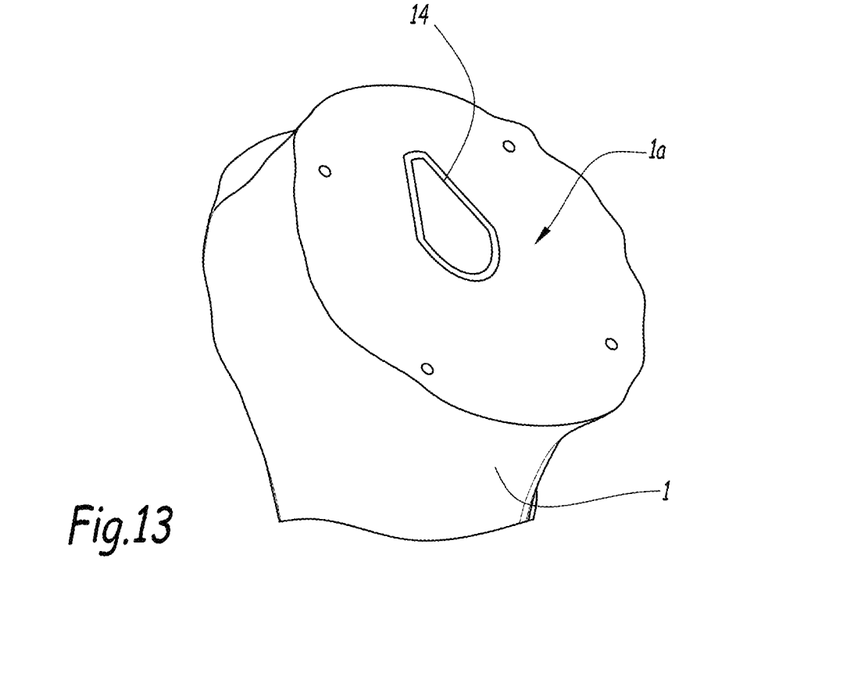
FIG. 13 is a perspective view of a humeral head with reference marks.

To this end, a positioning tool 10, represented on FIGS. 8 and 9, is provided. The positioning tool 10 comprises an inferior surface 100 and a superior surface 102. The inferior surface 100 is intended to be pressed against the resected surface 1a of the humeral head 1 and is provided with spiked pins 100a, adapted to house themselves in the cancellous bone 1c to lock in position the positioning tool 10 against the humeral head 1. The positioning tool 10 is provided with a central positioning hole 104. The positioning hole 104 has a shape complementary to the exterior shape of a reference punch 12. The reference punch 12 comprises a main body 120 provided with a superior surface 122 and an inferior surface 124 adapted to lay against the superior surface 102 of the positioning tool 10.

From the inferior surface 124 extends a protrusion 126 provided with a lateral contour 126a that is complementary to the shape of the hole 104. From the protrusion 126 extends an impacting body 128 which is formed by a tube having a transversal section matching the transversal section of the hollow stem 4 of the humeral implant 2. As represented on FIGS. 12 and 13, the positioning tool 10 is first impacted against the humeral head 1, then the reference punch 12 is mounted on the hole 104 of the positioning tool 10. The height H126 of the protrusion 126 substantially equals the thickness T10 of the positioning tool 10. The impacting body 128 is therefore inserted in the cancellous bone 1c during the mounting of the reference punch 12 in the positioning tool 10, leaving a positioning mark 14 in the resected surface 1a of the humeral head 1. The positioning mark 14 forms a contoured groove that matches the contour of the sharp edge 42 of the implant 2, allowing easier and accurate pre-positioning and successful impaction of the humeral implant 2.

Figure 14:
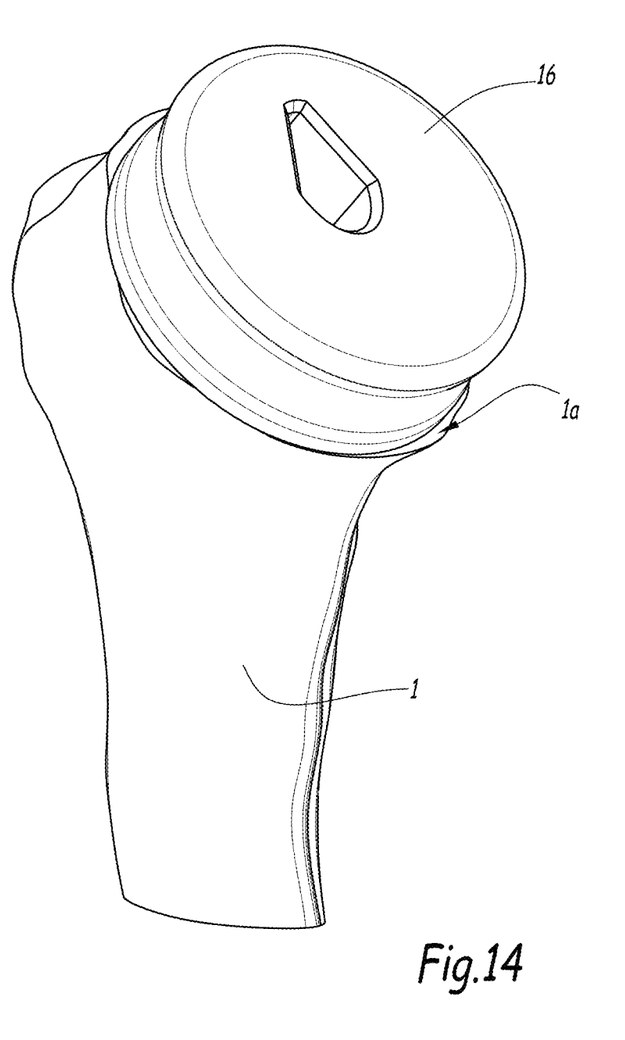
FIG. 14 is a perspective view of another embodiment of a punch used to create a reference mark.

In an alternative embodiment represented on FIG. 14, the positioning tool 10 and the reference punch 12 may be provided in a single tool 16 having spiked pins and an impacting body for directly providing the positioning mark on the resected surface 1a in a single operation.

The method allows providing a lighter humeral implant for the patient, due to the hollow feature of the humeral implant. The hollow feature of the humeral implant also allows savings on raw materials and weight of shipments.

The insertion of the cancellous bone 1c into the interior channel 40 allows cancellous bone preserving and a non-invasive technique.

The direct impaction of the humeral implant 2 in the cancellous bone allows time saving in operation room, as time for bone preparation is greatly reduced. The direct impaction also allows cost reduction on expensive patient-specific or ranges of compactor, rasps and cutting guides, and subsequent shipment weight and costs.

The use of additive manufacturing techniques allows savings on post machining operations, and makes possible specific implant shapes.

The invention claimed is:

1. A surgical shoulder articulation replacement method comprising:
   a) providing a humeral implant having a hollow stem, said hollow stem being provided with a sharp distal edge comprising a non-circular continuous periphery,
   b) making a reference mark comprising a non-circular continuous periphery on a cancellous bone of a humeral head of a patient, the reference mark corresponding to the desired location of impaction of the sharp distal edge of the hollow stem;
   c) aligning the non-circular continuous periphery of the sharp distal edge of the hollow stem with the non-circular continuous periphery of the reference mark;
   d) impacting the humeral implant in the cancellous bone of the humeral head of the patient at the desired location of impaction, with the sharp distal edge cutting the cancellous bone in the process.

2. Surgical method according to claim 1, wherein it further comprises a step comprising attaching an articulation member on the humeral implant.

3. Surgical method according to claim 1, wherein it comprises a further step, prior to step a), comprising determining the size and shape of the humeral implant using imaging.

4. Surgical method according to claim 3, wherein the size and shape of the humeral implant are determined using a CT scan or MRI.

5. Surgical method according to claim 1, wherein it comprises a step comprising providing an insertion guide adapted to guide the impaction of the humeral implant.

6. Surgical method according to claim 1, wherein prior to step b), the method comprises a step comprising making a cut in a cortical bone of the humeral head so as to uncover the cancellous bone.

7. Surgical method according to claim 1, wherein it comprises a further step comprising holding the humeral implant with a holding tool fixed to the humeral implant and having a handle.

8. Surgical method according to claim 7, wherein it comprises a further step comprising impacting the holding tool with a striking instrument.

9. Surgical method according to claim 1, wherein it comprises a further step comprising impacting the humeral implant with a striking instrument.

10. Surgical method according to claim 1, wherein it comprises a further step comprising impacting a detachable portion of the humeral implant with a striking instrument, then removing the detachable portion once the humeral implant is at its final place in the bone.

11. Surgical method according to claim 1, wherein it comprises a further step comprising providing a set of humeral implants of different sizes and shapes.

12. Surgical method according to claim 1, wherein the hollow stem has an ovoid cross section.

13. Surgical method according to claim 1, wherein the hollow stem of the humeral implant is pierced with transversal holes.

14. Surgical method according to claim 1, wherein the humeral implant is made by additive manufacturing.

15. Surgical method according to claim 1, wherein the humeral implant is manufactured in titanium or titanium alloy.

16. Surgical method according to claim 1, wherein the reference mark is provided by a reference punch matching the shape of the sharp distal edge of the hollow stem and adapted to create a groove in the bone.

17. A surgical shoulder articulation replacement method comprising:
   a) determining the size and shape of a humeral implant using imaging,
   b) providing the humeral implant with a hollow stem, said hollow stem having a sharp distal edge comprising a periphery,
   c) making a reference mark comprising an oblong continuous periphery on a cancellous bone of a humeral head of a patient, the oblong continuous periphery of the reference mark matching at least a portion of the periphery of the sharp distal edge of the hollow stem, the reference mark corresponding to the desired location of impaction of the sharp distal edge of the hollow stem;
   d) impacting the humeral implant in the cancellous bone of the humeral head of the patient at the desired location of impaction, with the sharp distal edge cutting the cancellous bone in the process.

18. Surgical method according to claim 17, wherein the hollow stem has an ovoid cross section.

19. A surgical shoulder articulation replacement method comprising:
   a) providing a humeral implant having a hollow stem and a mounting surface comprising a mounting hole, said hollow stem being provided with a sharp distal edge and an interior channel, the mounting hole of the humeral implant being in communication with the interior channel of the hollow stem to provide an open passage from a proximal end of the humeral implant to a distal end of the humeral implant;

b) impacting the humeral implant in a cancellous bone of a humeral head of a patient, with the sharp distal edge cutting the cancellous bone in the process.

20. Surgical method according to claim 19, wherein the hollow stem has a circular cross section.

* * * * *

UNITED STATES PATENT AND TRADEMARK OFFICE
CERTIFICATE OF CORRECTION

Page 1 of 1

PATENT NO. : 10,898,348 B2
APPLICATION NO. : 15/835110
DATED : January 26, 2021
INVENTOR(S) : Willy Vivanz et al.

It is certified that error appears in the above-identified patent and that said Letters Patent is hereby corrected as shown below:

In the Specification

In Column 4, Line 41, delete "embodiment" and insert --embodiments--.

In Column 4, Line 44, delete "Win" and insert --W in--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*